(12) United States Patent
Georis

(10) Patent No.: US 9,261,471 B2
(45) Date of Patent: Feb. 16, 2016

(54) DEVICE FOR MEASURING UREA CONCENTRATION

(75) Inventor: Philippe Lucien Valmy Georis, Chelles (FR)

(73) Assignee: Inergy Automotive Systems Research (Societe Anonyme), Brussels (BE)

( * ) Notice: Subject to any disclaimer, the term of this patent is extended or adjusted under 35 U.S.C. 154(b) by 0 days.

(21) Appl. No.: 14/130,825

(22) PCT Filed: Jul. 4, 2012

(86) PCT No.: PCT/EP2012/063055
§ 371 (c)(1),
(2), (4) Date: Jan. 13, 2014

(87) PCT Pub. No.: WO2013/004755
PCT Pub. Date: Jan. 10, 2013

(65) Prior Publication Data
US 2014/0132951 A1    May 15, 2014

(30) Foreign Application Priority Data
Jul. 4, 2011    (EP) .................................... 11172508

(51) Int. Cl.
*G01N 21/41* (2006.01)
*G01N 25/00* (2006.01)
(Continued)

(52) U.S. Cl.
CPC .............. *G01N 25/00* (2013.01); *F01N 11/00* (2013.01); *G01N 21/41* (2013.01); *G01N 21/43* (2013.01); *F01N 2560/14* (2013.01); *F01N 2610/02* (2013.01); *F01N 2610/1406* (2013.01);
(Continued)

(58) Field of Classification Search
USPC ................... 356/72, 128, 445, 432, 436, 437; 250/339.01, 341.8; 73/114.19; 60/287, 60/274
See application file for complete search history.

(56) References Cited

U.S. PATENT DOCUMENTS 5,548,393 A * 8/1996 Nozawa et al. ................. 356/70
8,542,353 B2 * 9/2013 Christian et al. .............. 356/128
(Continued)

FOREIGN PATENT DOCUMENTS

DE    102011089703 B3 *  5/2013
EP       1 048 340        11/2000
(Continued)

OTHER PUBLICATIONS

International Search Report Issued Oct. 26, 2012 in PCT/EP12/063055 Filed Jul. 4, 2012.
(Continued)

Primary Examiner — Sang Nguyen
(74) Attorney, Agent, or Firm — Oblon, McClelland, Maier & Neustadt, L.L.P.

(57) ABSTRACT

A device for monitoring a urea solution in a tank of a motor vehicle tank includes a light source capable of emitting a light beam, a photodetector capable of detecting a portion of a light beam emitted by the light source, and a part made of a material allowing the propagation of a light beam emitted by the light source. The part includes a surface intended to be in contact with the urea solution. The light source, the photodetector, and the part are arranged in such a way that a light beam emitted by the light source is propagated by the surface of the part, by refraction, toward the photodetector. A tank including such a monitoring device is provided. A process for monitoring a urea solution in a tank of a motor vehicle is also provided.

13 Claims, 1 Drawing Sheet

(51) Int. Cl.
  *F01N 11/00* (2006.01)
  *G01N 21/43* (2006.01)

(52) U.S. Cl.
  CPC . *F01N2900/1818* (2013.01); *G01N 2021/4153* (2013.01); *G01N 2021/434* (2013.01); *Y02T 10/47* (2013.01)

(56) References Cited

U.S. PATENT DOCUMENTS

| | | | |
|---|---|---|---|
| 2003/0025909 A1* | 2/2003 | Hallstadius | 356/436 |
| 2007/0208238 A1* | 9/2007 | Harjunmaa et al. | 600/316 |
| 2008/0265145 A1* | 10/2008 | Uchida | 250/226 |
| 2009/0015822 A1* | 1/2009 | Uchida et al. | 356/135 |
| 2010/0084558 A1* | 4/2010 | Wang et al. | 250/339.11 |
| 2010/0218484 A1* | 9/2010 | Arlt et al. | 60/274 |
| 2010/0294021 A1* | 11/2010 | Makino et al. | 73/25.03 |
| 2010/0327884 A1* | 12/2010 | McCall et al. | 324/682 |
| 2011/0192149 A1* | 8/2011 | Yasui | 60/287 |
| 2011/0247319 A1* | 10/2011 | Konno | 60/286 |

FOREIGN PATENT DOCUMENTS

| | | |
|---|---|---|
| EP | 2 098 698 | 9/2009 |
| JP | 2001 020724 | 1/2001 |
| JP | 2005 257319 | 9/2005 |
| WO | 2008 107336 | 9/2008 |

OTHER PUBLICATIONS

European Search Report Issued Oct. 28, 2011 EP 11 17 2508 Filed Jul. 4, 2011.

* cited by examiner

DEVICE FOR MEASURING UREA CONCENTRATION

BACKGROUND OF THE INVENTION

1. Field of the Invention

The present invention relates to the monitoring of a liquid, in particular a liquid contained in a tank of an SCR (Selective Catalytic Reduction) system in a motor vehicle, the liquid being an aqueous urea solution.

2. Description of the Related Art

Legislation on vehicle and heavy goods vehicle emissions stipulates, amongst other things, a reduction in the release of nitrogen oxides NOx into the atmosphere. One known way to achieve this objective is to use the SCR process which enables the reduction of nitrogen oxides by injection of a reducing agent, generally ammonia, into the exhaust line. This ammonia may derive from the thermolytic decomposition of an ammonia precursor solution, whose concentration may be the eutectic concentration. Such an ammonia precursor is generally a urea solution (eutectic at 32.5% by weight of urea).

With the SCR process, the high discharge of NOx produced in the engine during combustion at optimized efficiency are treated in a catalyst as they exit the engine. This treatment requires the use of the reducing agent at a precise concentration and of extreme quality. The solution is thus accurately metered and injected into the exhaust gas stream where it is hydrolysed before converting the nitrogen oxide (NOx) to nitrogen (N2) and water (H2O).

To do this, it is necessary to equip the vehicles with a tank containing an additive solution (generally aqueous urea solution).

However, it is important to be able to monitor the quality of the reducing agent in the tank to be able to dose it in an accurate manner.

BRIEF SUMMARY OF THE INVENTION

The invention notably has the aim of providing a simple and efficient device making it possible to monitor the quality of an aqueous urea solution in a storage tank.

With this aim, the subject of the invention is a device for monitoring a urea solution in a tank of a motor vehicle, characterized in that it comprises a light source capable of emitting a light beam, a photodetector capable of detecting a portion of a light beam emitted by the light source and a part made of a material allowing the propagation of a light beam emitted by the light source, the part having a surface intended to be in contact with the urea solution, the light source, the photodetector and the part being arranged in such a way that a light beam emitted by the light source is propagated by the surface of the part, by reflection or by refraction, toward the photodetector.

Using the device, it is possible to monitor simply and very quickly the presence and the quality of the urea solution in the tank. Indeed, when the light source emits a light beam in the part, the beam is first propagated to the surface of the part in contact with the urea solution defining an interface between the part and the solution. At this interface, the beam is partly reflected in the part and partly refracted in the urea solution. The intensity of the reflected beam and the angle of the refracted beam depend on the refractive index of the part, on the presence or otherwise of urea solution in the tank and, in the event of the urea solution being present, on the urea solution itself (notably its concentration, which in fact determines the refractive index of the solution). As the material of the part is unchanged, the intensity of the reflected beam and the angle of the refracted beam depend essentially on the presence of the urea solution and, in this case, on the concentration of urea in the solution. Thus, ignoring the case where the tank is empty, the photodetector detects a portion of the propagated light beam of which either the intensity (case of the reflected beam) or the angle (case of the refracted beam) varies as a function of the concentration of urea in the solution.

This device is simple, compact, cheap and reliable because it does not contain any moving components. It makes it possible to monitor whether the tank is empty and, if it contains a urea solution, whether the concentration of urea in the solution is in accordance with what it should be.

The monitoring device can furthermore consist in one or a plurality of the following characteristics, taken alone or in combination. The device can comprise means for measuring the temperature. It is thus possible to take into account the evolution of the refractive index of the part and of the urea solution with temperature.

The light source can be a light-emitting diode (LED). The LED is robust, economical and consumes little energy. An LED can be chosen that emits light in a narrow range of wavelengths in order to reduce the phenomena of decomposition of the light at the interface between the part and the urea solution and to obtain a more accurate signal.

The photodetector can be a photodiode. This type of photodetector is simple and converts the light it absorbs into an electrical signal. This signal can be easily used.

The part can be made of a mineral material, glass or quartz for example. These materials offer a good chemical resistance vis-a-vis the urea solution and allow a good propagation of the emitted light beam.

The device can comprise a semi-transparent mirror, preferably incorporated into the part and capable of separating a light beam emitted by the light source into two beams of different trajectories, namely a first light beam, not deviated by the mirror and which is propagated by the surface of the part toward the photodetector and a second control light beam, reflected by the mirror and propagated toward a second control photodetector. Using this control light beam detected by a control photodetector, it is possible to take into account the evolution of the measurement conditions, which are independent of the concentration of urea but likely to influence the detection by the photodetector, notably of the temperature of the urea solution and of the aging of the light source.

The light source and the photodetector are preferably incorporated into the part. Indeed, when these elements are outside the part, it is necessary to handle multiple reflections. Moreover, this variant offers advantages of compactness and adjustment. When possible, depending on the nature of the materials, this incorporation can be done by overmolding. This incorporation makes it possible to reduce tolerances, simplify fabrication etc. Another configuration would be to have the photodetector sunk directly into the solution but then a specific positioning device would be necessary.

The part may be angled or be in two components which allows (on the condition of an adequate arrangement of the light source and the photodetector) for the production of a double refraction and hence an increase (multiplication by two) in the accuracy of the measurement.

Another subject of the invention is a tank for storing a urea solution in a motor vehicle, characterized in that it comprises a device as defined previously.

Advantageously, the device is borne by the lower wall of the tank. The term "lower wall of the tank" is understood to mean the wall that is closest to the ground when the tank is mounted on the vehicle. This positioning of the device makes it possible to ensure that the device is most often in contact with the urea solution.

By "borne" we mean that either the device rests on this wall, or that the part of the device is sunk (passes) through this wall, which avoids having to make the electrical connections pass through said wall.

Another subject of the invention is a process for monitoring a urea solution in a tank of a motor vehicle, characterized in that it comprises the following steps:

emission of a light beam in a part made of a material allowing the propagation of said beam and having a surface intended to be in contact with the urea solution and by which said beam is propagated by reflection and by refraction, measurement of a physical quantity characterizing a light beam propagated (reflected or refracted) by the surface of the part and comparison of the quantity with a reference value.

It will be noted that the characterizing physical quantity of the propagated light beam can be compared to several reference values, or even to a range of reference values.

Generally, this physical quantity is either the intensity of the propagated beam if the latter is reflected, or the angle of the propagated beam if the latter is refracted.

The process can comprise an additional step consisting in a measurement of the temperature of the urea solution. In this case, the comparison takes the measured temperature into account.

The process can also comprise two additional steps consisting in:

a separation of the emitted light beam into two beams of different trajectories, namely a first light beam propagated by the surface of the part and a second control light beam reflected by a mirror, and a measurement of a characterizing quantity of the control light beam.

In this case, the comparison takes into account the characterizing quantity of the control light beam. Preferably, the mirror used is a semi-transparent mirror as described above.

The process can also comprise a step of detection of the immobility of the vehicle and a step of detection of the filling of the tank, the light beam being emitted by the light source when the two conditions are verified. Thus, the monitoring is for example performed intermittently, when the driver of the vehicle turns on the ignition after having filled the urea tank.

Finally, in a preferred variant, the part is angled and the light source and the photodetector are incorporated into this part and arranged so as to produce a double refraction, as explained previously.

BRIEF DESCRIPTION OF THE SEVERAL VIEWS OF THE DRAWINGS

The invention will be better understood on reading the following description, given solely by way of example and made with reference to the drawings in which.

DETAILED DESCRIPTION OF THE INVENTION

Figure 1:
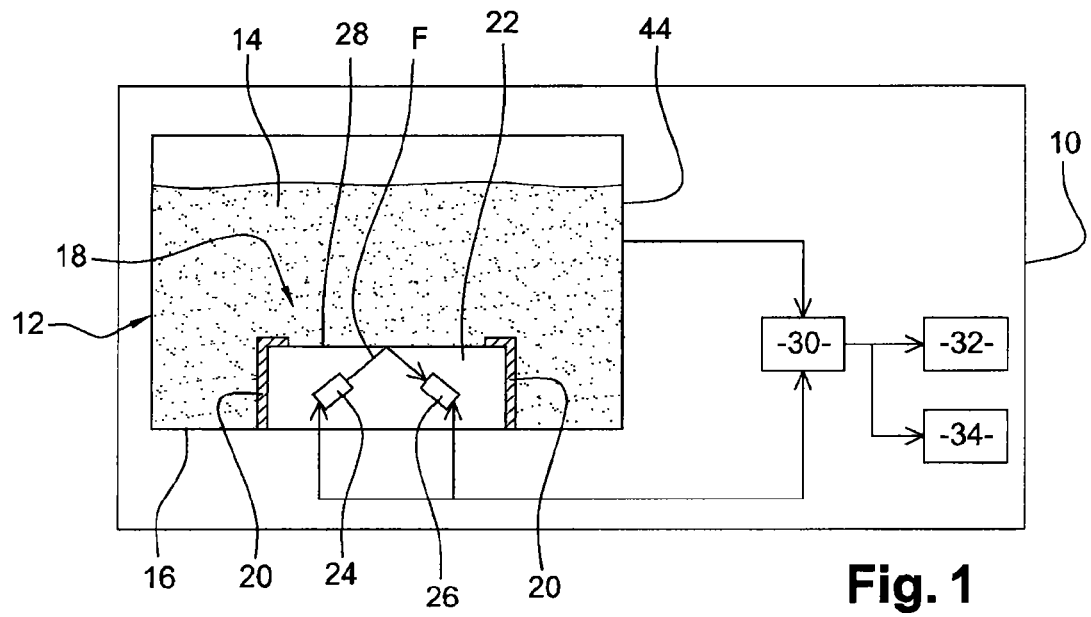
FIG. 1 is a schematic representation of a motor vehicle comprising a device for monitoring the urea solution in a tank, according to a first embodiment of the invention

FIG. 1 shows a motor vehicle 10 comprising a tank 12 containing an aqueous urea solution 14. The aqueous urea solution 14 has a concentration of urea of around 32.5% by weight (eutectic composition).

The tank 12 is generally of substantially parallelepipedal shape and comprises a lower wall 16 which bears a monitoring device 18 immersed in the urea solution 14. The device 18 can be fixed by clipping means 20 onto the lower wall 16. It can also be welded, bonded or fixed to it using other fixing means.

The monitoring device 18 comprises a part 22 made of a material allowing the propagation of light. The part 22 can, for example, be made of a mineral material, such as glass or quartz, which are materials which are not attacked by the urea solution 14 and which allow a good propagation of light. The part 22 comprises a light source 24 and a photodetector 26. At least one surface 28 of the part 22 is in contact with the urea solution 14 and materializes an interface between the part 22 and the urea solution 14. The light source 24 can be an LED and the photodetector 26, a photodiode.

In this embodiment, the light source 24 is arranged in the part 18 in such a way as to emit a light beam F toward the surface 28 of the part 22. The photodetector 26 is arranged in the part 22 so that it can detect the reflected portion of the beam when the beam emitted by the light source meets the surface 28.

In FIG. 1, a micro-computer 30, an error light 32 and an engine 34 of the motor vehicle 10 are also shown.

It should be noted that the representation of the various constituent items in the figures is not proportional. Indeed, the volume of the tank 12 is generally between 3 and 30 liters whereas the volume of the device 18 is less than 20 cm$^3$, or even less than 10 cm$^3$.

Given these proportions, it is understood that the surface 28, although lying on the upper section of the part 22, is situated on the bottom of the tank 12, i.e. in proximity to its lower wall lying closest to the ground when the tank is mounted on the vehicle 10.

The process for monitoring the urea solution 14 contained in the tank 12 of this embodiment will be described.

When we wish to monitor the quality of the urea solution 14, i.e. to ensure that the concentration of urea of the solution is definitely that of the eutectic, the light source 24 emits a light beam F toward the surface 28 of the part 22. The beam propagates into the material of the part 22. When it reaches the surface 28 of the part 22 in contact with the urea solution 14, a portion of the beam is refracted in the solution 14 and a portion is reflected into the part 18. The reflected portion of the beam propagates into the material of the part 22 and is detected by the photodetector 26. In the remainder of the text, "reflected beam" denotes the portion of the beam reflected by the surface 28 of the part.

According to the concentration of the urea solution, the intensity of the reflected beam detected by the photodetector 26 varies. In the embodiment described, we use this quantity, namely the intensity of the reflected beam, to characterize the light beam detected by the photodetector 26.

The intensity of the reflected beam is converted by the photodetector 26 into an electrical signal which is sent to the micro-computer 30. The micro-computer 30 compares the quantity received from the photodetector 26 to a reference value or to a set of reference values defining a range of reference values considered as acceptable for the correct operation of the SCR system.

If the quantity received from the photodetector 26 does not lie in the range of reference values, the micro-computer 30 sends an error signal to the error light 32. The error light 32 can be a pilot light or a sonic alarm which warns the driver of the vehicle that the tank of urea 10 is empty or that the concentration of urea in the aqueous urea solution is not in accordance.

Furthermore, the micro-computer 30 can also be connected to the engine 34 of the motor vehicle and, in the event of an anomaly being detected, send a signal which prevents the vehicle 10 from starting. The signal sent by the micro-computer 30 can also limit the engine 34 power and limit the speed of the vehicle, for example to 50 km/h, thus making it possible to move the vehicle to a breakdown site, even if the SCR system is not functioning correctly.

Advantageously, the monitoring of the quality of the urea solution 14 contained in the tank 12 is carried out when the vehicle 10 is immobile and the tank 10 has just been partly or completely filled. It is possible to automate the monitoring of the urea solution 14 when these two conditions are met, particularly when the driver of the vehicle has just filled the tank 10 and is turning on the ignition.

For example, when starting the vehicle, the vehicle is stopped, the micro-computer 30 can monitor whether the level of the filling gauge 44 of the tank 10 has varied significantly from a value recorded when the ignition was turned off and, if so, launch the process for monitoring the urea solution 14.

Figure 2:
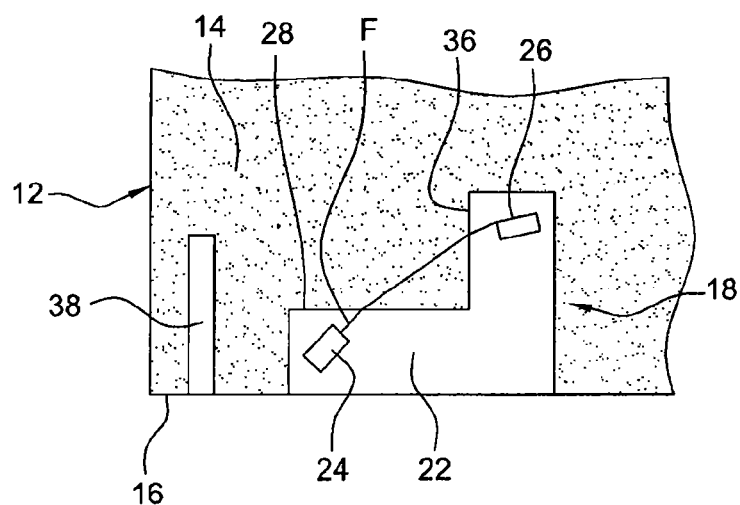
FIG. 2 is a partial cut-away view of a tank and of a monitoring device, according to a second embodiment of the invention.
Figure 3:
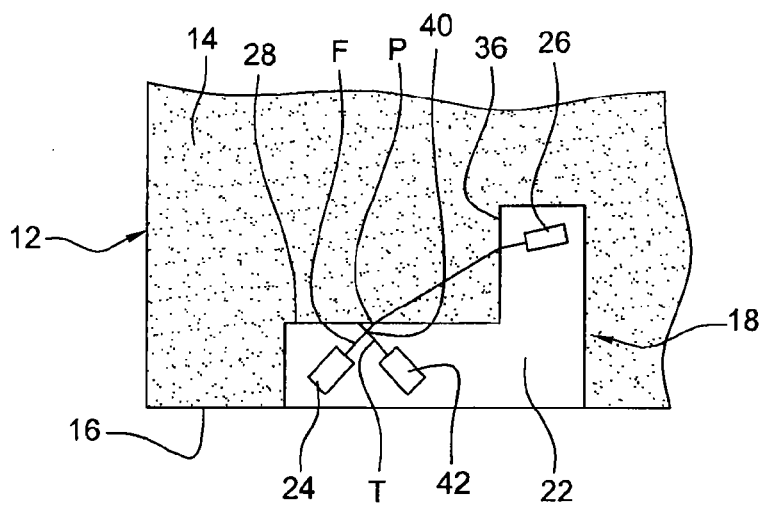
FIG. 3 is a view similar to the view in FIG. 2, according to a third embodiment of the invention.

In FIGS. 2 and 3 are shown a second and a third embodiment of a monitoring device according to the invention, in which the elements common to the various embodiments are identified by the same reference numbers, although arranged differently with respect to each other.

In the embodiment in FIG. 2, the beam F emitted by the light source 24 reaches the surface 28 of the part 22 where a portion of the beam is refracted. In the remainder of the text, "refracted beam" denotes the refracted portion of the incident beam. The refracted beam propagates into the urea solution 14 and reaches a second surface 36 of the part 22 in contact with the urea solution 14, where it is refracted again. The doubly refracted beam is then detected by the photodetector 26.

Preferably, the light source 24 is positioned in order to emit a light beam forming an angle of around 60° with the normal to the surface 28 and the photodetector 26 is positioned at an angle of around 70° with respect to the normal to the surface 36. In this configuration, the beam detected by the photodetector 26 is nil if the surfaces 28 and 36 are not in contact with the urea solution 14.

If the concentration of the urea solution 14 is modified, the beam is deviated and the photodetector 26 detects a light beam of differing intensity.

Although the beam emitted by the light source is 24 is refracted a first time at the solid-liquid interface formed by the surface 28 of the part 22 in contact with the urea solution 14, then a second time at the liquid-solid interface formed by the surface 36 of the part 22 in contact with the urea solution 14, the refracted beam detected by the photodetector 26 is of good quality. Indeed, the portion of the beam refracted at the interface between the part 22 and the urea solution 14 represents over 95% of the beam emitted by the light source 24; there is therefore little signal loss. Quite to the contrary, in this embodiment, the fact that the light beam detected by the photodetector undergoes a double refraction multiplies by two the sensitivity of the device to the variation in concentration of the urea solution, which increases its precision.

In the second embodiment in FIG. 2, the device also comprises means for measuring the temperature 38, for example a temperature probe.

When monitoring the urea solution 14 in the tank 12, the refracted beam is detected by the photodetector 26 which transforms the received signal into an electrical signal, which is, for example, supplied to a micro-computer 30 similar to that shown in FIG. 1. The micro-computer 30 also receives a signal emitted by the temperature probe 38 and takes this data into account when comparing the received quantity from the photodetector 26 and the reference value or range of reference values. It is therefore possible to take the temperature variation into account.

It is understood that the temperature measurement means 38 are not limited to a temperature probe. Furthermore, the temperature measurement means 38 can also be present in the embodiment shown in FIG. 1.

In the third embodiment in FIG. 3 is shown a device similar to that in FIG. 2, but which furthermore comprises a semi-transparent mirror 40 (schematized on this figure, but which is preferably a plate bearing a coating and oriented at 45° so that one half of the incident beam simply passes through it while the other half is reflected) which separates the beam F emitted by the light source 24 into two beams of different trajectories. A first light beam P is propagated into the material of the part 22, without being deviated from its initial trajectory, toward the surface 28 where it is refracted in the urea solution and is detected by the photodetector 26, as in the second embodiment. A second control light beam T is propagated in the material of the part 22 and reflected by the mirror toward a second control photodetector 42.

The control light beam T only propagates in the material of the part 22. The signal that it detects makes it possible to take into account parameters of evolution of the measurement, such as the aging of the light source 24 and the temperature of the urea solution 14. The taking into account of the temperature by the control photodetector 42 is justified by the fact that the device 18 is immersed in the urea solution 14 and that it is of small volume compared to the volume of the urea solution 14 in the tank 12. It can therefore be hypothesized that the temperature of the device 18 and that of the urea solution 14 are the same.

When one desires to monitor the quality of the urea solution 14 in the tank, the comparison of the received quantity from the photodetector 26 with a reference value or a range of reference values takes into account the characterizing quantity of the light beam detected by the control photodetector 42 and transmitted to the micro-computer 30.

It is of course understood that the invention is not limited to the embodiments previously described.

For example, the first embodiment can comprise means 38 for measuring the temperature, the comparison between the characterizing quantity of the light beam transmitted by the surface 28 of the part 22 with a reference value or a set of reference values defining a range of reference values taking the measured temperature into account.

The device 18 of the second and third embodiments can be connected to a micro-computer 30 of the motor vehicle 10, as shown in FIG. 1.

The invention claimed is:

1. A device for monitoring a urea solution in a tank of a motor vehicle, comprising:
    a light source to emit a light beam,
    a photodetector to detect a portion of a light beam emitted by the light source, and
    a part made of a material allowing propagation of the light beam emitted by the light source, the part including a surface intended to be in contact with the urea solution,
    the light source, the photodetector, and the part being arranged in such a way that the light beam emitted by the light source is propagated by the surface of the part, by refraction, toward the photodetector, the light source being arranged in such a way that the propagated light beam includes an angle that varies as a function of a concentration of urea, and the part being made of a mineral material, including glass or quartz.

2. The device as claimed in claim 1, comprising a temperature probe to measure the temperature.

3. The device as claimed in claim 1, comprising a semi-transparent mirror to separate the light beam emitted by the light source into two beams of different trajectories, namely a first light beam propagated by the surface of the part toward the photodetector and a second control light beam propagated toward a second control photodetector.

4. The device as claimed in claim 1, wherein the light source and the photodetector are incorporated into the part.

5. The device as claimed in claim 4, wherein the part is angled and in which the light source and the photodetector are arranged in such a way as to produce a double refraction of the light beam emitted by the light source.

6. A tank for storing a urea solution in a motor vehicle comprising a device as claimed in claim 1, said device being borne by a lower wall of the tank.

7. The tank as claimed in claim 6, wherein the device is sunk through the lower wall of the tank.

8. A process for monitoring a urea solution in a tank of a motor vehicle, comprising:
    emitting a light beam in a part made of a material allowing propagation of said light beam and including a surface intended to be in contact with the urea solution and by which said light beam is propagated by refraction,
    measuring a physical quantity characterizing the light beam propagated by the surface of the part, and
    comparing the quantity with a reference value.

9. The monitoring process as claimed claim 8, wherein the physical quantity is an angle of the propagated beam.

10. The monitoring process as claimed in claim 8, further comprising measuring a temperature of the urea solution, and in which the comparing takes the measured temperature into account.

11. The monitoring process as claimed in claim 8, further comprising
    separating the emitted light beam into two beams of different trajectories, namely a first light beam propagated by the surface of the part and a second control light beam reflected by a mirror, and
    measuring a characteristic quantity of the control light beam, and in which the comparing takes into account the characteristic quantity of the control light beam.

12. The monitoring process as claimed in claim 8, further comprising detecting immobility of the vehicle and detecting filling of the tank, the light beam being emitted by a light source when these two detecting conditions are verified.

13. The monitoring process as claimed in claim 8, wherein the part is angled and a light source and a photodetector are incorporated into this part and arranged so as to produce a double refraction.

* * * * *